United States Patent
Jeon et al.

(10) Patent No.: US 11,906,457 B2
(45) Date of Patent: Feb. 20, 2024

(54) LIGHT-ACTIVATED GAS SENSOR BASED ON 3D NANOSTRUCTURE OPERABLE AT LOW TEMPERATURE WITH HIGH PERFORMANCE AND METHOD FOR MANUFACTURING THE SAME

(71) Applicant: KOREA ADVANCED INSTITUTE OF SCIENCE AND TECHNOLOGY, Daejeon (KR)

(72) Inventors: Seokwoo Jeon, Daejeon (KR); Donghwi Cho, Daejeon (KR); Youngsuk Shim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 143 days.

(21) Appl. No.: 17/403,389

(22) Filed: Aug. 16, 2021

(65) Prior Publication Data
US 2022/0057353 A1  Feb. 24, 2022

(30) Foreign Application Priority Data
Aug. 18, 2020 (KR) ........................ 10-2020-0103418

(51) Int. Cl.
*G01N 27/12* (2006.01)
*G01N 33/00* (2006.01)

(52) U.S. Cl.
CPC ......... *G01N 27/128* (2013.01); *G01N 27/125* (2013.01); *G01N 33/0027* (2013.01)

(58) Field of Classification Search
CPC . G01N 27/128; G01N 27/125; G01N 33/0027
See application file for complete search history.

(56) References Cited

FOREIGN PATENT DOCUMENTS

| KR | 10-2012-0021647 A | 3/2012 |
|---|---|---|
| KR | 10-1358098 B1 | 2/2014 |
| KR | 10-1362481 B1 | 2/2014 |
| KR | 101611133 B1 * | 4/2016 |
| KR | 10-1829120 B1 | 2/2018 |

OTHER PUBLICATIONS

Nasiri et al., "Nanostructured Gas Sensors for Medical and Health Applications: Low to High Dimensional Materials", Mar. 17, 2019, Biosensors 2019, 9, 43, 1-22 (Year: 2019).*
Chang et al. "Fabrication and gas sensing properties of hollow SnO2 hemispheres," Chemical Communications, Jul. 21, 2009, pp. 4019.
(Continued)

*Primary Examiner* — Feba Pothen
(74) *Attorney, Agent, or Firm* — Womble Bond Dickinson (US) LLP

(57) ABSTRACT

A gas sensor includes a first electrode disposed on a substrate, a second electrode disposed on the substrate and spaced apart from the first electrode, and a sensitive member disposed on the substrate. The sensitive member contacts first and second electrodes and has a porous structure from a three-dimensional (3D) arrangement of shells including a gas-sensitive material. A thickness of the sensitive member is 5 μm to 10 μm, and a thickness of the shells is 10 nm to 40 nm.

4 Claims, 13 Drawing Sheets

(56) References Cited

OTHER PUBLICATIONS

Chi-Jung Chang et al., "Gas sensors with porous three-dimensional framework using TiO2/polymer double-shell hollow microsphere", Thin Solid Films, 2011, vol. 520, pp. 1546-1553.
Jun Min Suh, et al. "Synergetically Selective Toluene Sensing in Hematite-Decorated Nickel Oxide Nanocorals," Advanced Materials Technologies, 2, pp. 1600259 (2017).
Song et al. "Downsizing gas sensors based on semiconducting metal oxide: Effects of electrodes on gas sensing properties," Sensors and Actuators B: Chemical, 248, pp. 949 (2017).
Ziyue Zhang et al., "Ultrasensitive ppb-level NO2 gas sensor based on WO3 hollow nanosphers doped with Fe", Applied Surface Science, 434, pp. 891-897, (2018).

* cited by examiner

LIGHT-ACTIVATED GAS SENSOR BASED ON 3D NANOSTRUCTURE OPERABLE AT LOW TEMPERATURE WITH HIGH PERFORMANCE AND METHOD FOR MANUFACTURING THE SAME

CROSS-REFERENCE TO RELATED APPLICATION

This application claims priority to and benefits of Korean Patent Application No. 10-2020-0103418 under 35 U.S.C. § 119 filed on Aug. 18, 2020 in the Korean Intellectual Property Office, the entire contents of which are incorporated herein by reference.

BACKGROUND

1. Technical Field

The invention relates to a gas sensor. More particularly, the invention relates to a light-activated gas sensor based on a three-dimensional (3D) nanostructure, which operates at a low temperature with high performance, and a method for manufacturing the light-activated gas sensor.

2. Description of the Related Art

A recently commercialized gas sensor technology outputs a sensing signal corresponding to an electrical resistance change by adsorption/desorption reaction of a metal oxide surface having a sensitive characteristic when exposed to a specific gas. Specifically, the resistance change-based gas sensor type operates through thickness modulation of an electron depletion layer formed by gas adsorption on a surface of a metal oxide semiconductor constituting a sensitive material. Therefore, a size of the specific surface area of the sensitive material, a material capable of increasing the specific surface area of the sensitive material and a method for activating the sensitive material may be important in determining a sensor sensitivity.

In order to improve the sensor sensitivity, research from various material perspectives, such as building an one-to-one matched sensor material library according to detection factors and researching its nanostructure, is being conducted. However, when a scale of the structure is reduced, a sensor sensitivity and a sensor durability may be deteriorated because inflow and flow of gas are inhibited. Furthermore, when a sensitive material is heated for activation, there are difficulties such as energy consumption and limited integration with other modules. Therefore, it is necessary to consider not only nanostructure to improve sensitivity, but also a gas-mechanical approach to fabricate a structure advantageous in introducing gas and a method for activating a sensitive material.

A conventional sensor may be operable at a high temperature of 300° C. or more in order to activate a sensitive material. It may bring problems such as high energy consumption and fundamental difficulty of integration with an electronic device such as smartphones, smart electronic products or the like. In order to overcome the above problems, a sensor that is activated by light to operate at a room temperature is being developed. However, the light-activated sensor is still difficult to be effectively applied to a sensor because of absence of a structure that can effectively use light, low sensitivity, requirement for light (ultraviolet light) with high energy to increase sensitivity, small reaction speed or the like or the like.

SUMMARY

One object of the invention is to provide a gas sensor that includes a 3D nanostructure with periodicity and may be effectively light-activated and can operate at a room temperature with high performance.

Another object of the invention is to provide a method for manufacturing the gas sensor.

According to an embodiment of the invention, a gas sensor includes a first electrode disposed on a substrate, a second electrode disposed on the substrate and spaced apart from the first electrode, and a sensitive member disposed on the substrate. The sensitive member contacts the first and second electrodes and has a porous structure with three-dimensional (3D) arrangement of shells including a gas-sensitive material. A thickness of the sensitive member is 5 μm to 10 μm, and a thickness of the shells is 10 nm to 40 nm.

In an embodiment, the gas-sensitive material includes a metal oxide semiconductor.

In an embodiment, the metal oxide semiconductor includes at least one of $SnO_2$, $ZnO$, $WO_3$, $Fe_2O_3$, $Fe_3O_4$, $NiO$, $TiO_2$, $CuO$, $In_2O_3$, $Zn_2SnO_4$, $Co_3O_4$, $PdO$, $LaCoO_3$, $NiCo_2O_4$, $Ca_2Mn_3O_8$, $V_2O_5$, $Ag_2V_4O_{11}$, $Ag_2O$, $MnO_2$, $InTaO_4$, $InTaO_4$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$ and $Ba_{0.5}Sr_{0.5}Co_{0.8}Fe_{0.2}O_3$-δ.

In an embodiment, a porosity of the sensitive member is 90% or more.

According to an embodiment of the invention, a detention system includes the gas sensor and a light source irradiating a light to the gas sensor to activate the sensitive member.

According to an embodiment of the invention, a method for manufacturing a gas sensor is provided. According to the method, a first electrode and a second electrode spaced apart from the first electrode are formed on a substrate. An adhesive film is formed to have an opening that overlaps a gap between the first and second electrodes and partially overlaps the first and second electrodes. A photoresist film is formed on the adhesive film, the first electrode, the second electrode and the substrate. A three-dimensionally distributed light is provided to the photoresist film to form a 3D porous structure in a first area of the photoresist film, which overlaps the gap between the first and second electrodes and partially overlaps the first and second electrodes, and to form a solid structure without pores in a second area of the photoresist film, which is adjacent to the first area.

According to embodiments of the invention, a 3D porous sensitive member may have an increased specific surface area and an increased porous distribution, which means that nano-pores and micro-pores exist therein. Thus, an effective surficial gas reaction may be possible, and penetration and diffusion of a gas may be increased. Furthermore, the 3D porous sensitive member has a light-scattering structure similar to an optical maze thereby amplifying a light incident thereon. Thus, a metal oxide semiconductor may be more effectively light-activated so that a sensitivity of the sensor may be remarkably increased.

According to embodiments, a 3D nanostructure including a sensitive material may be integrated selectively on a substrate through an optical patterning method without limitation due to a complicated sensor structure. Furthermore, a sensor array capable of multiple-detection may be manufactured and massively produced, and the method may be compatible with conventional MEMS (Micro Electric Mechanical System) technologies.

Furthermore, the 3D porous sensitive member may be activated by a low energy light (near ultraviolet ray to visible ray). Thus, high performance may be achieved at a room temperature.

DETAILED DESCRIPTION OF THE EMBODIMENTS

Figure 1:
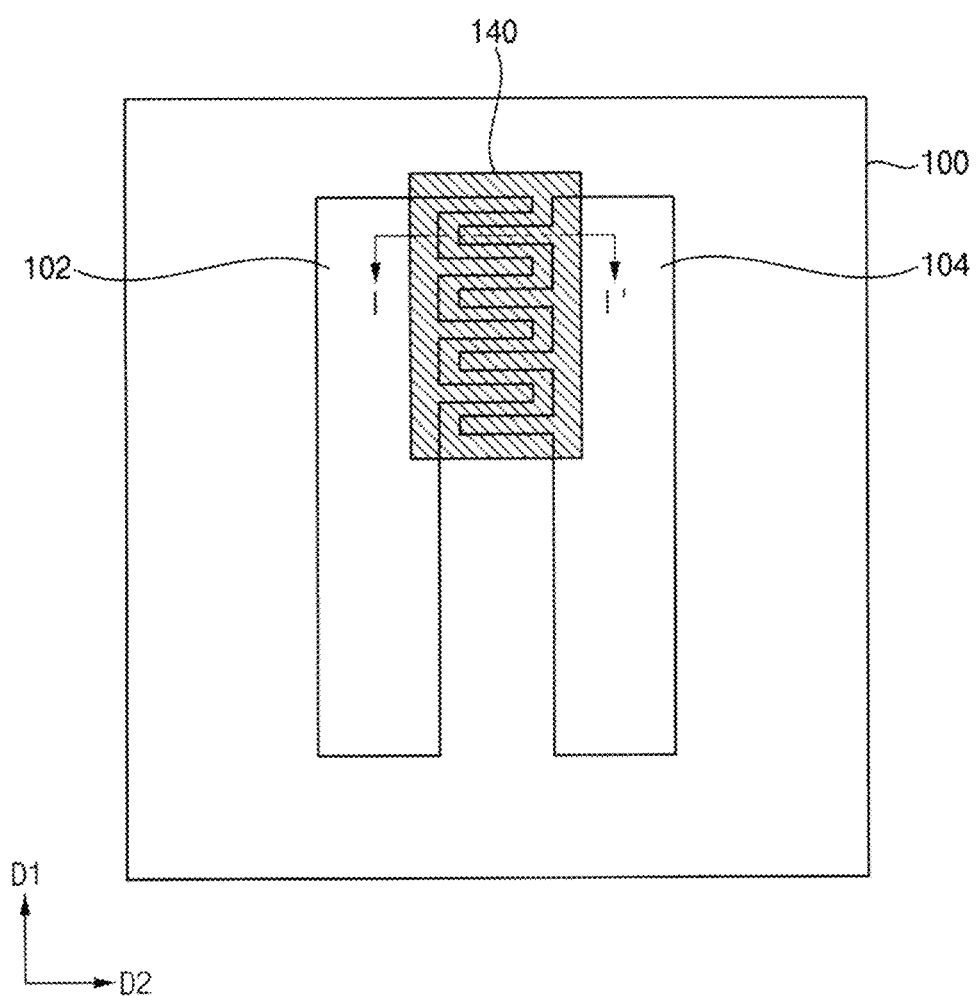
FIG. 1 is a plan view illustrating a gas sensor according to an embodiment of the present invention.

Various embodiments will be described more fully hereinafter with reference to the accompanying drawings, in which some embodiments are shown. The invention may, however, be embodied in many different forms and should not be construed as limited to the embodiments set forth herein. Rather, these embodiments are provided so that this description will be thorough and complete, and will fully convey the scope of the invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a," "an" and "the" are intended to include a plurality of forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
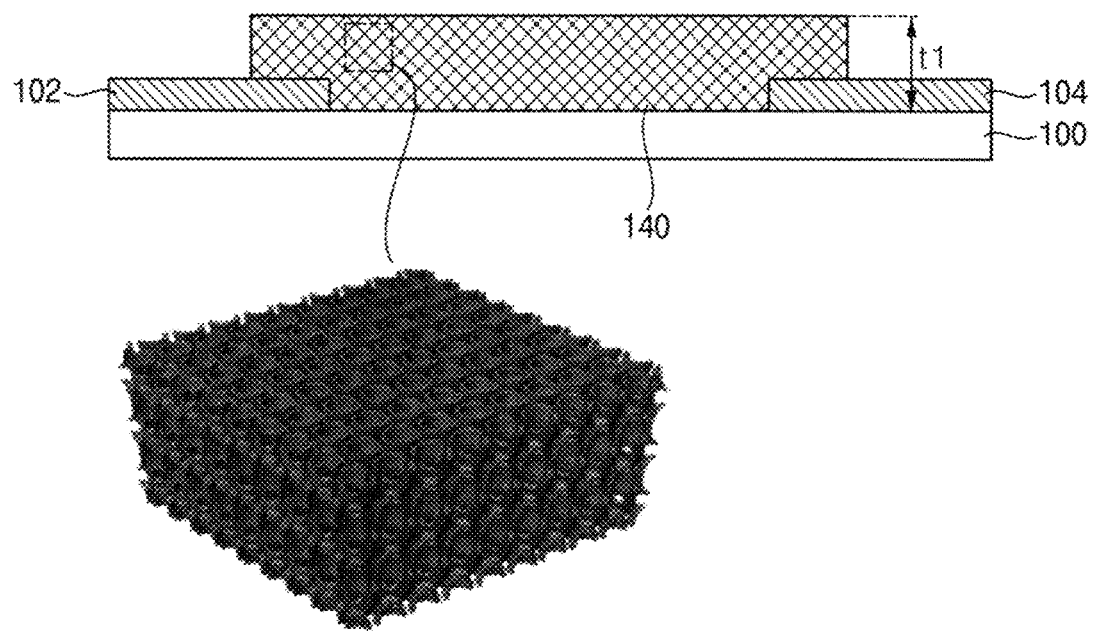
FIG. 2 is a cross-sectional view taken along line I-I' of FIG. 1.

FIG. 1 is a plan view illustrating a gas sensor according to an embodiment of the present invention. FIG. 2 is a cross-sectional view taken along line I-I' of FIG. 1.

Referring to FIGS. 1 and 2, a gas sensor according to an embodiment includes a first electrode 102, a second electrode 104 spaced apart from the first electrode 102 and a three-dimensional (3D) porous sensitive member 140 including a gas-sensitive material and having a 3D nanostructure. The 3D porous sensitive member 140 may contact the first electrode 102 and the second electrode 104. The first electrode 102, the second electrode 104 and the 3D porous sensitive member 140 may be disposed on a substrate 100. In an embodiment, the 3D porous sensitive member 140 may contact upper surfaces of the first electrode 102 and the second electrode 104.

For example, the substrate 100 may include a metal, silicon, glass, quartz or the like. Furthermore, the substrate 100 may have a stacked structure including a non-conductive substrate and a conductive layer.

The first electrode 102 and the second electrode 104 include a conductive material. For example, the first electrode 102 and the second electrode 104 may include gold (Au), silver (Ag), copper (Cu), aluminum (Al), cobalt (Co), nickel (Ni), titanium (Ti), chromium (Cr), platinum (Pt), palladium (Pd), indium tin oxide, indium zinc oxide or a combination thereof, and may have a single-layered structure or a multi-layered structure.

The first electrode 102 and the second electrode 104 may be arranged alternately in an area overlapping the 3D porous sensitive member 140. For example, the first electrode 102 and the second electrode 104 may each include a plurality of protrusions extending in a first direction D1 and arranged in a second direction D2 perpendicular to the first direction D1.

The 3D porous sensitive member 140 may include various materials having sensitive characteristics to be applicable for a gas sensor. For example, the 3D porous sensitive member 140 may include a metal oxide semiconductor. For example, the metal oxide semiconductor may include $SnO_2$, ZnO, $WO_3$, $Fe_2O_3$, $Fe_3O_4$, NiO, $TiO_2$, CuO, $In_2O_3$, $Zn_2SnO_4$, $Co_3O_4$, PdO, $LaCoO_3$, $NiCo_2O_4$, $Ca_2Mn_3O_8$, $V_2O_5$, $Ag_2V_4O_{11}$, $Ag_2O$, $MnO_2$, $InTaO_4$, $InTaO_4$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, $Ba_{0.5}Sr_{0.5}Co_{0.8}Fe_{0.2}O_3$-δ or a combination thereof. Preferably, the 3D porous sensitive member 140 may include a sensitive material that may be activated by light. In an embodiment, the 3D porous sensitive member 140 may include $TiO_2$.

The 3D porous sensitive member 140 may have an ordered 3D structure with periodicity. In an embodiment, the 3D porous sensitive member 140 may have a nano-shell structure. For example, the 3D porous sensitive member 140 may have a structure in which a plurality of shells defining an inner pore therein are 3-dimensionally arranged, and inner pores in adjacent shells may be connected to each other. Furthermore, pores may be further defined between adjacent shells.

In an embodiment, a thickness t1 of the 3D porous sensitive member 140 may be about 1 μm to about 30 μm, and preferably about 5 μm to about 10 μm. When a thickness t1 of the 3D porous sensitive member 140 is excessively large, a portion, where a gas enters and diffuses mostly, is too far from the electrodes thereby reducing a sensitivity of the sensor. When a thickness t1 of the 3D porous sensitive member 140 is excessively small, an amount of the sensitive material is reduced thereby reducing a sensitivity of the sensor.

A thickness of the shells may be about 10 nm to about 100 nm, and preferably about 10 nm to about 40 nm. When a thickness of the shells is excessively large, porosity is reduced thereby reducing penetration and diffusion of a gas. When a thickness of the shells is excessively small, an amount of the sensitive material is reduced thereby reducing a sensitivity of the sensor. For example, porosity (volume ratio) of the 3D porous sensitive member 140 may be about 90% or more.

The 3D porous sensitive member 140 may have an increased specific surface area and an increased porous distribution, which means that nano-pores and micro-pores exist therein. Thus, an effective surficial gas reaction may be possible, and penetration and diffusion of a gas may be increased. Furthermore, the 3D porous sensitive member 140 has a light-scattering structure similar to an optical maze thereby amplifying a light incident thereon. Thus, a metal oxide semiconductor may be more effectively light-activated so that a sensitivity of the sensor may be remarkably increased.

According to embodiments, a 3D nanostructure including a sensitive material may be integrated selectively on a substrate through an optical patterning method without limitation due to a complicated sensor structure. Furthermore, a sensor array capable of multiple-detection may be manufactured and massively produced, and the method may be compatible with conventional MEMS (Micro Electric Mechanical System) technologies.

Furthermore, the 3D porous sensitive member 140 may be activated by a low energy light (near ultraviolet ray to visible ray). Thus, high performance may be achieved at a room temperature.

A detection system according to an embodiment may include the gas sensor and a light source providing a light to the gas sensor.

FIGS. 3, 4, 5, 6, 7, 8 and 9 are cross-sectional views illustrating a method for manufacturing a gas sensor according to an embodiment of the present invention. FIGS. 3 to 9 may show a same cross-section as that illustrated in FIG. 2.

Figure 3:
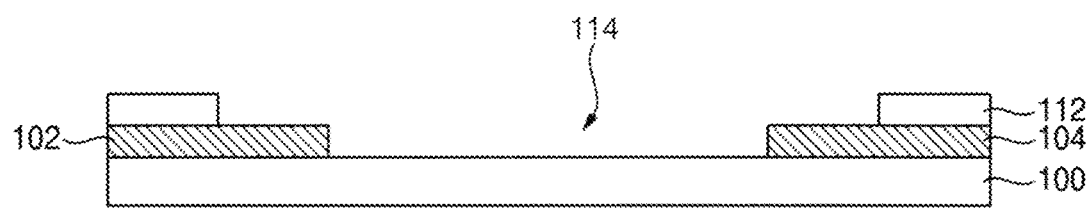
FIGS. 3, 4, 5, 6, 7, 8 and 9 are cross-sectional views illustrating a method for manufacturing a gas sensor according to an embodiment of the present invention.

Referring to FIG. 3, a first electrode 102 and a second electrode 104 spaced apart from the first electrode 102 are formed on a substrate 100.

Thereafter, an adhesive film 112 is formed on the substrate 100 and the first and second electrodes 102 and 104. For example, the adhesive film 112 may include an opening 114. The opening 114 may overlap portions of the first and second electrodes 102 and 104 and an upper surface of the substrate 100, which is exposed between the first and second electrodes 102 and 104.

The adhesive film 112 may include a photoresist material. For example, a first photoresist material may be coated on the substrate 100 through a spin coating process. The first photoresist material coated on the substrate 100 may be preliminarily heated (soft-baked), for example, at about 90° C. to about 100° C. Thereafter, the coated layer may be light-exposed with a portion, which corresponds to the opening 114, being masked, and then developed to remove the masked portion thereby forming the opening 114. For example, the coated layer may be light-exposed by UV ray or the like. Thereafter, the coated layer may be hard-baked on a hot plate at about 100° C. to about 250° C. thereby forming the adhesive film 112.

Figure 4:
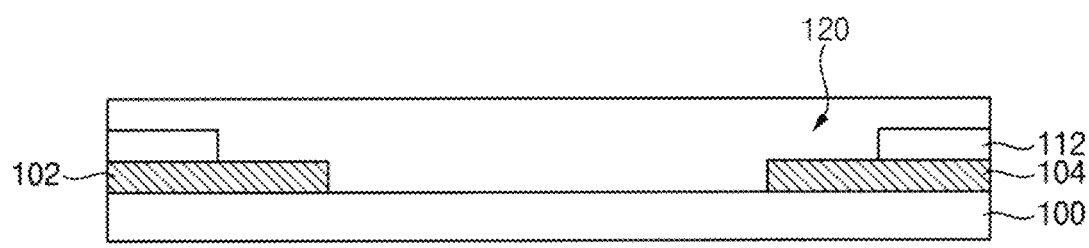

Referring to FIG. 4, a photoresist film 120 is formed on the adhesive film 112. The photoresist film 120 may fill the opening 114 to contact the substrate 100 and the first and second electrodes 102 and 104.

In an embodiment, a second photoresist material may be coated on the adhesive film 112, an exposed upper surface of the substrate 100 and exposed upper surfaces of the first and second electrodes 102 and 104 through a spin coating process. The second photoresist material coated on the substrate 100 may be soft-baked, for example, at about 90° C. to about 100° C. to form the photoresist film 120.

The first photoresist material and the second photoresist material for forming the adhesive film 112 and the photoresist film 120 may include a same composition or different compositions from each other. In an embodiment, the first photoresist material or the second photoresist material may include an epoxy-based negative-tone photoresist composition, or a DNQ-based positive-tone photoresist composition. In some embodiments, the first photoresist material or the second photoresist material may include an organic-inorganic hybrid material, hydrogel, a phenolic resin or the like, which can be cross-linked by light exposure.

In an embodiment, the adhesive film 112 may have a thickness of about 0.5 μm to about 5 μm. The photoresist film 120 may have a thickness of about 0.3 μm to about 1 mm, and may preferably have a thickness of about 1 μm to about 100 μm.

Figure 5:
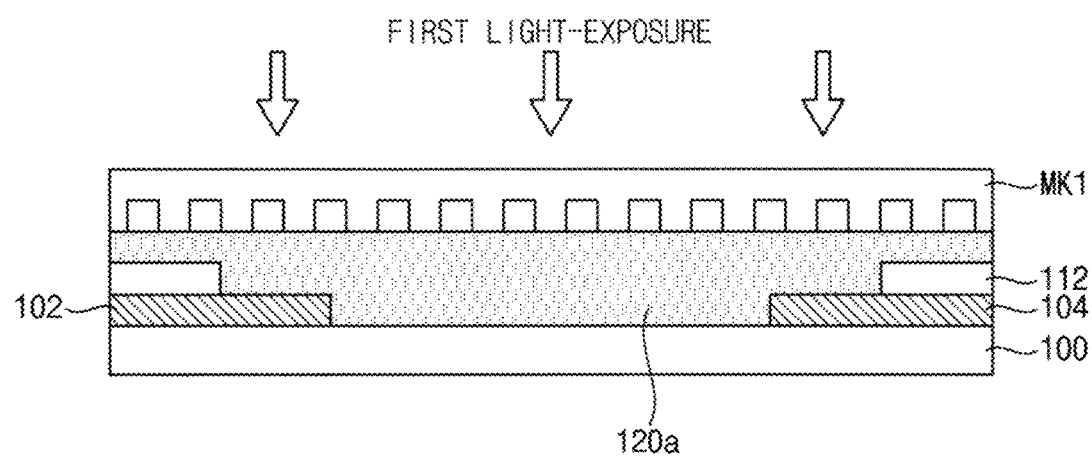

Referring to FIG. 5, the photoresist film 120 is exposed to a light. In an embodiment, a three-dimensionally distributed light is provided to the photoresist film 120 for a first light-exposure process.

The three-dimensional light-exposure may be performed by proximity-field nano-patterning (PnP) method.

In PnP method, a light is irradiated onto a phase mask MK1 including an elastomer material and a periodic uneven pattern. A light passing through the phase mask MK1 is periodically three-dimensionally distributed by interference effect. Thus, the photoresist film 120 may be three-dimensionally exposed to a light. For example, the phase mask MK1 may have a convexo-concave lattice structure formed at a surface, through which a light passes, and may include a flexible elastomer material. When the phase mask MK1 contacts the photoresist film, the phase mask MK1 may spontaneously adhere to or conformal-contact a surface of the photoresist film 120 by Van der Waals force.

For example, when a laser having a wavelength similar to a periodicity of the lattice-of the phase mask MK1 is irradiated onto the phase mask MK1, a three-dimensionally distributed light may be formed by Talbot effect. When the photoresist film 120 is formed from a negative-tone photoresist composition, cross-linking of a resin may be selectively caused in a portion where light intensity is relatively high by constructive interference, and may be hardly caused in a remaining portion where light intensity is relative low. Thus, the remaining portion, which is barely or not light-exposed, may be removed in a developing process. As a result, a porous polymeric structure having a three-dimensional porous network with a periodicity of hundreds of nanometers to several micrometers. After the developing process, the photoresist film may be dried.

In an embodiment, a pore size and a periodicity of the porous polymeric structure may be adjusted depending on a wavelength of the laser and a design of the phase mask MK1.

More detailed explanation of the PnP method are disclosed in J. Phys. Chem. B 2007, 111, 12945-12958; Proc. Natl. Acad. Sci. U.S.A. 2004, 101, 12428; Adv. Mater. 2004, 16, 1369; and Korean Patent Publication 2006-0109477, which are incorporated herein for references.

In an embodiment, the phase mask MK1 used in the PnP process may include a material such as PDMS (polydimetyl siloxane), PUA (polyurethane acrylate), PFPE (perfluoropolyether) or the like.

Figure 6:
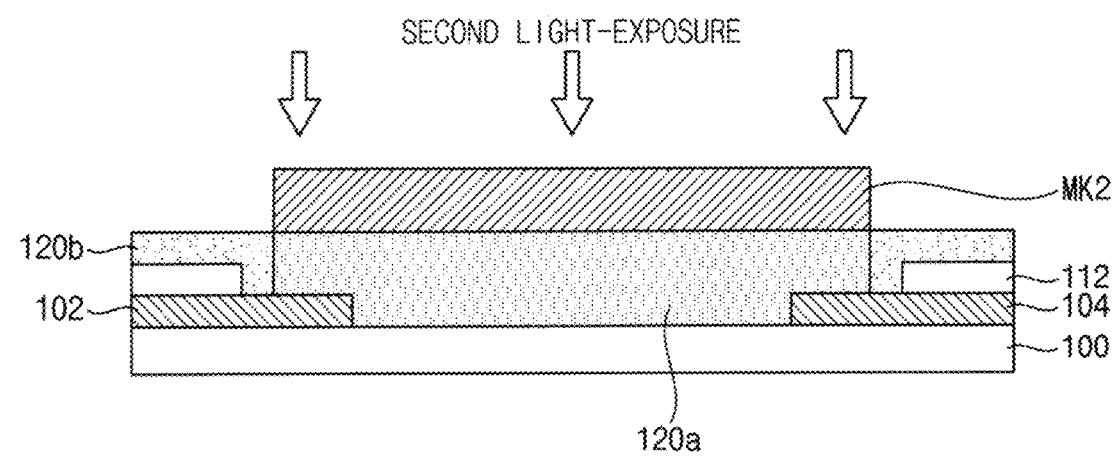

Referring to FIG. 6, while a portion 120a of the three-dimensionally light-exposed photoresist film is masked, a second light exposure process is performed. For example, a light-blocking mask MK2 is disposed on a first area overlapping portions of the first and second electrodes 102 and 104 and a gap between the first and second electrodes 102 and 104, and a remaining area may be exposed to a light. As a result, a portion 120b of the photoresist film disposed in a second area adjacent to the first area may be entirely exposed to a light.

Figure 7:
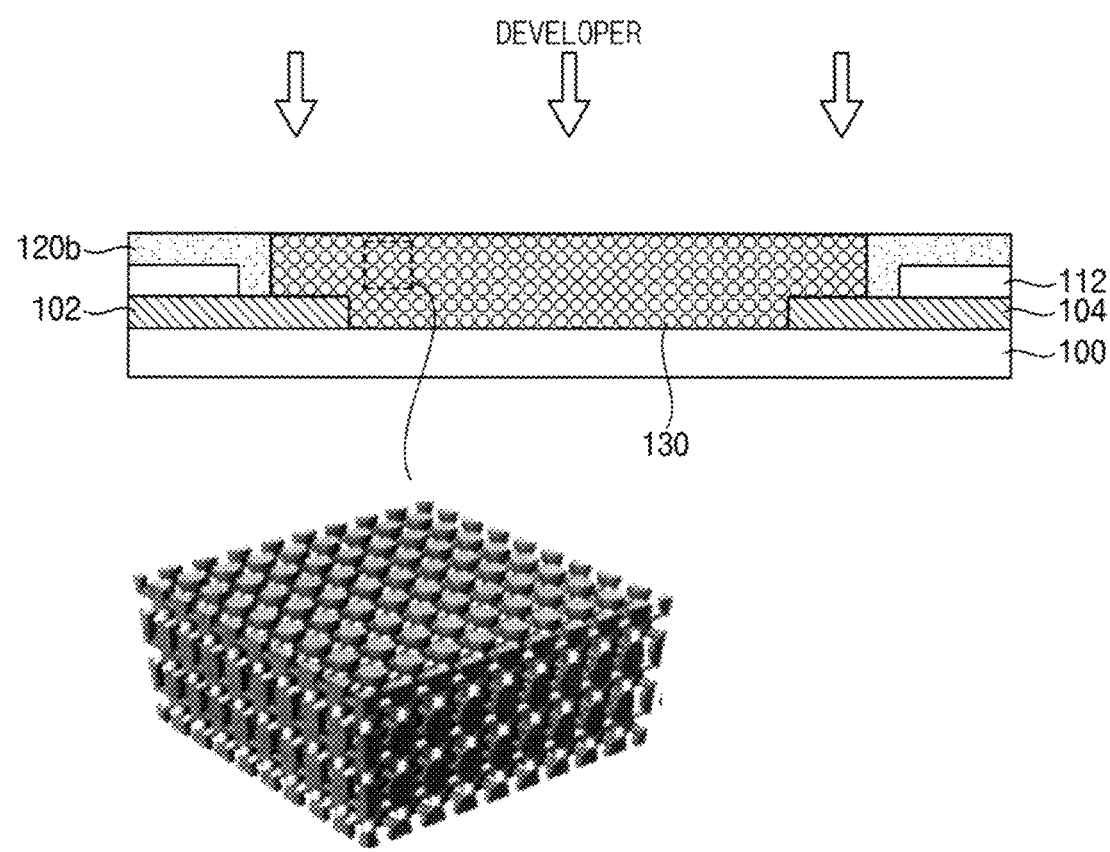

Referring to FIG. 7, the photoresist film 120b is developed. In an embodiment, when the photoresist film 120b is formed from a negative-tone photoresist composition, a non-light-exposed portion may be removed by a developer, and a light-exposed portion may remain. As a result, a 3D porous template 130 including a 3D nano-pore network may be formed on the substrate 100. The portion 120b of the photoresist film 120, which is exposed to a light in the second light-exposure process, may be entirely cross-linked to have a solid structure without pores. For example, the developer may include propylene glycol monomethyl ether acetate (PGMEA).

For example, the 3D porous template 130 include channels formed by nano-scaled pores in a range of about 1 nm to about 2,000 nm, which are three-dimensionally connected to each other entirely or partially. Thus, the 3D porous template 130 may have a 3D network structure periodically distributed by the channels.

Figure 8:
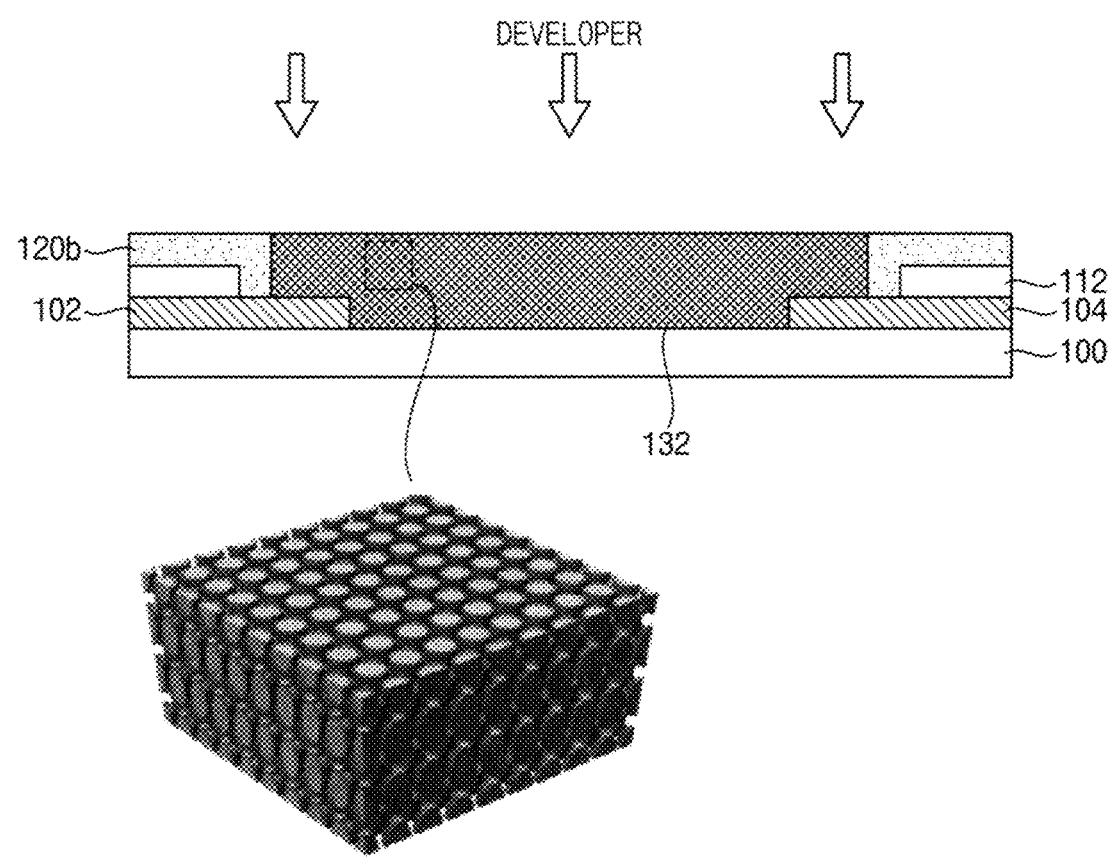

Referring to FIG. 8, a sensitive material is provided in the pores (channels) of the 3D porous template 130 to form a composite 132 having a 3D shell structure of the sensitive material.

In an embodiment, the sensitive material may be provided in the 3D porous template 130 through deposition method such as atomic layer deposition (ALD), chemical vaporization deposition (CVD) or the like. However, embodiments are not limited thereto, and various methods such as plating, liquid process or the like, which are known to provide a material in a porous structure, may be used.

The portion 120b of the photoresist film in the second area may function as preventing contraction of the 3D porous template 130 along a horizontal direction in a deposition process performed at a high temperature. Thus, uniformity and reliability of the 3D shell structure may be improved.

Thereafter, the 3D porous template is removed to form a 3D porous sensitive member 140.

In an embodiment, the 3D porous template may be removed through heat treatment, wet etching or plasma treatment.

The heat treatment may be performed at about 400° C. to about 1,000° C., for example, at an atmosphere including air or oxygen gas. Furthermore, inert gas such as argon (Ar) may be added to the atmosphere.

The plasma treatment may include oxygen-plasma treatment or reactive ion etching (RIE).

The 3D porous sensitive member 140 may have an inverse structure of the 3D porous template. Thus, the 3D porous sensitive member 140 may have a porous structure including pores (channels), which are three-dimensionally connected to each other.

Figure 9:
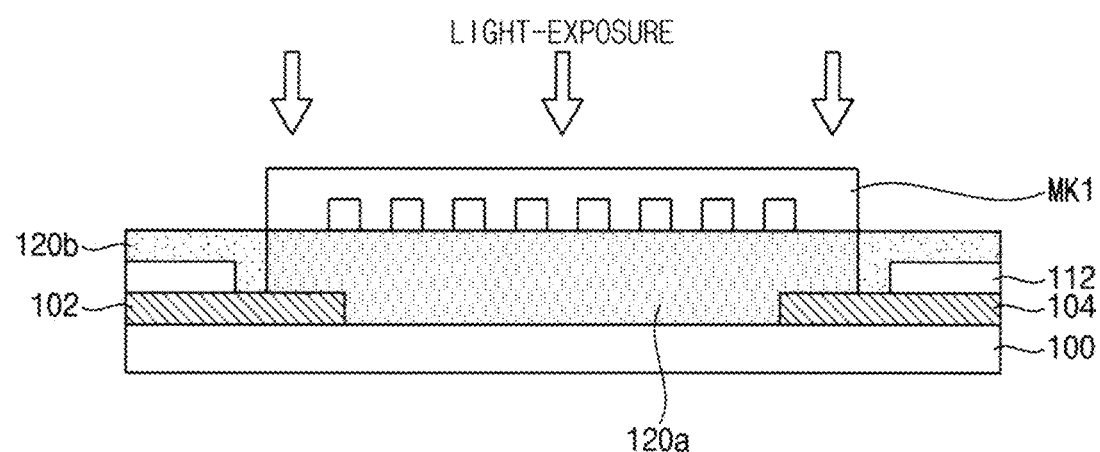

In an embodiment, a three-dimensional light-exposed portion (first area) and a full light-exposed portion (second area) of a photoresist film may be formed in a single light-exposure process. For example, as illustrated in FIG. 9, when a phase mask MK1 is disposed on a photoresist film to selectively overlap a first portion 120a of the photoresist film, a second portion 120b of the photoresist film may be fully light-exposed to form a solid structure.

Hereinafter, effects and manufacturing methods of gas sensors according to embodiments will be explained with reference to following examples. However, the following examples and experiments are provided as examples for explanation, and embodiments of the present invention are not limited thereto.

Example 1: Manufacturing Gas Sensor Including 3D Porous Sensitive Member

A photoresist composition (trade name: SU-8 2, manufactured by Micro Chem) was spin-coated on an Si substrate with Pt electrodes for 30 seconds by 3,000 rpm to form a photoresist film having a thickness of 2 μm. Edges of the Pt electrodes were masked by a tape for evaluating sensor characteristics. The substrate with the photoresist film was heated on a hot plate at 65° C. for 10 minutes and at 95° C. for 10 minutes. Thereafter, a chrome mask was disposed on the photoresist film, and the photoresist film was exposed to a UV lamp of 365 nm for 1 minute (100 mJ/cm$^2$), and heated at 120° C. for 3 minutes to cross-link a photoresist material in a portion unmasked by the chrome mask. Thereafter, the photoresist film was developed by a developer and rinsed by ethanol to form an adhesive film having an opening exposing the Pt electrodes.

Thereafter, a photoresist composition (SU-8 10) was spin-coated by 1,000 rpm to 3,000 rpm to vary a thickness of a photoresist film from 2 μm to 30 μm, and heated on a hot plate at 65° C. for 1 hour and at 95° C. for 2 hours to form a photoresist film.

A phase mask formed of PDMS and having a convexo-concave surface with a periodically arranged rectangular lattice was disposed to contact the photoresist film. An Nd:YAG laser was irradiated to the photoresist film through the phase mask to exposed the photoresist film to a three-dimensionally distributed light.

Thereafter, in order to selectively form a 3D nanostructure and to reduce physical defects between the electrodes and the 3D nanostructure, while a portion of the photoresist film overlapping a gap between the Pt electrodes and the Pt electrodes adjacent to the gap was masked, a remaining portion of the photoresist film was further exposed to a light and was heated at 65° C. for 6 minutes. Thereafter, the photoresist film was developed in a developer for 30 minutes, rinsed by ethanol for 30 minutes and dried to form the 3D nanostructure (3D porous template) selectively on the electrodes.

Thereafter, $TiO_2$, which is a sensitive material, was deposited in the 3D porous template, and the adhesive film and the 3D porous template were removed by plasma etching and heat treatment to form a 3D porous sensitive member contacting the Pt electrodes.

According to the above, gas sensors with various deposition thicknesses (shell thicknesses) and film thicknesses were prepared, and experiments were performed to measure and evaluate characteristics thereof. In the experiments, a voltage of a light source (LED) was 5.0V, and a gas concentration was 5 ppm.

Figure 10:
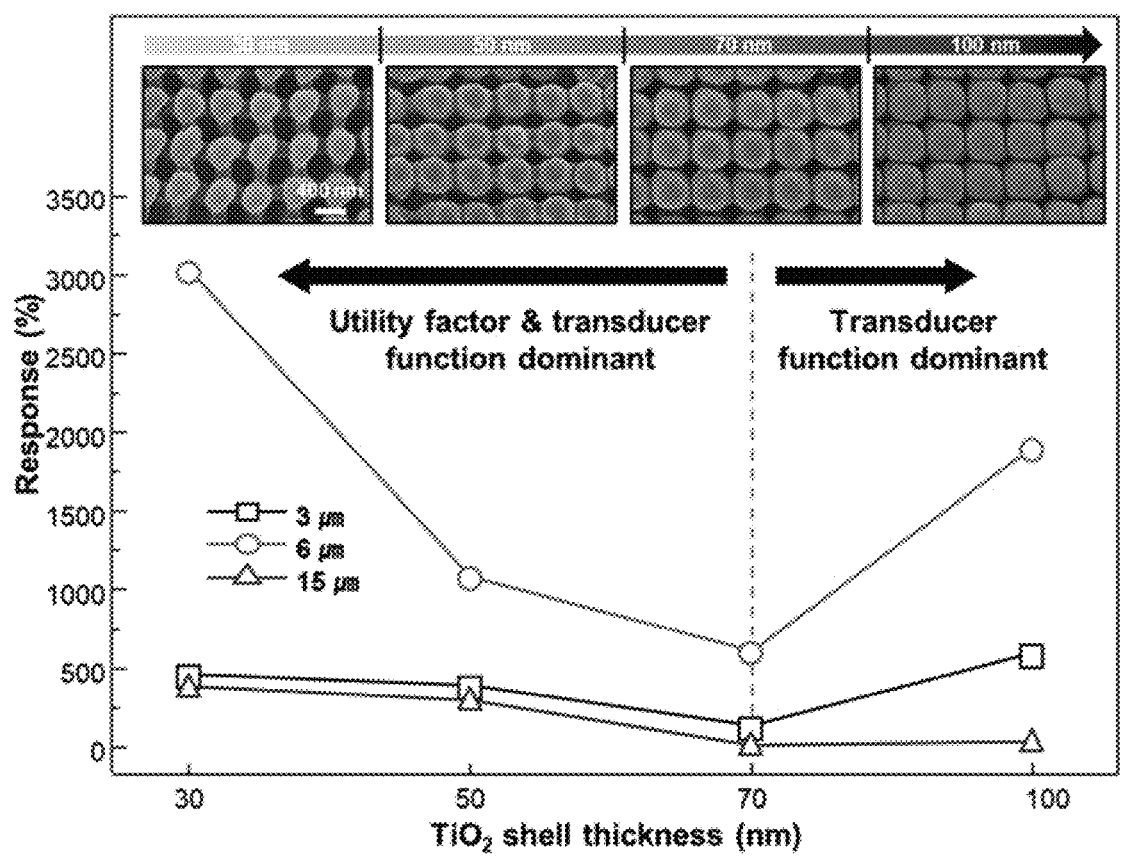
FIG. 10 shows scanning electron microscope (SEM) images showing the 3D porous sensitive members of Examples depending on shell thicknesses of $TiO_2$ and a graph showing responses to $NO_2$ of the gas sensors of Examples depending on shell thicknesses and film thicknesses of the 3D porous sensitive members.

FIG. 10 shows scanning electron microscope (SEM) images showing the 3D porous sensitive members of Examples depending on shell thicknesses of $TiO_2$ and a graph showing responses to $NO_2$ of gas sensors depending on shell thicknesses and film thicknesses of the 3D porous sensitive members Referring to FIG. 10, when a shell thickness was less than 50 nm, a response of the gas sensors was highest due to utility factor. However, when a shell thickness was more than 70 nm, a response of the gas sensors was increased due to transducer function.

Figure 11:
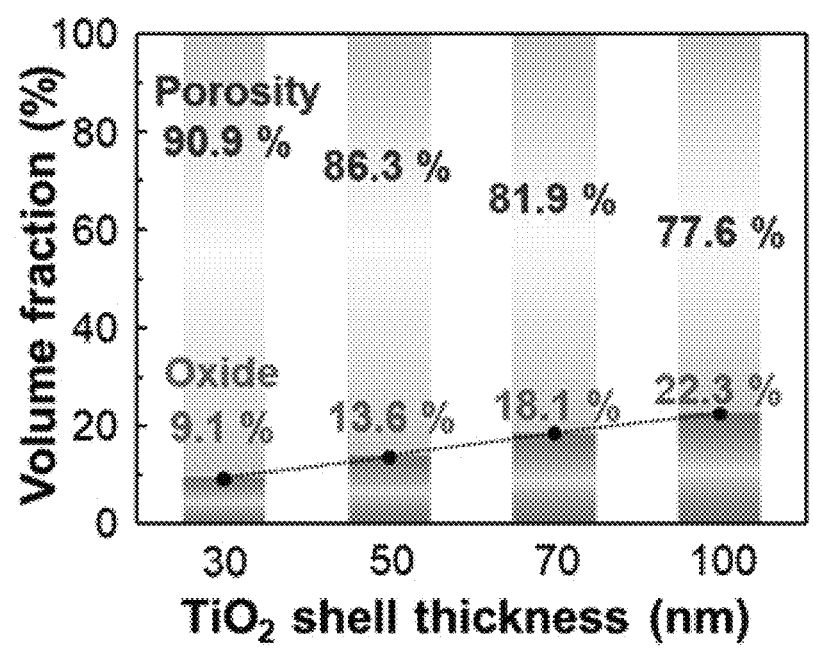
FIG. 11 is a graph showing a porosity and a volume fraction of the 3D porous sensitive members of Examples on shell thicknesses of $TiO_2$.

FIG. 11 is a graph showing a porosity and a volume fraction of the 3D porous sensitive members of Examples on shell thicknesses of $TiO_2$.

Referring to FIG. 11, it can be noted that a porosity of a 3D porous sensitive member is reduced as a shell thickness of $TiO_2$ is increased.

Figure 12:
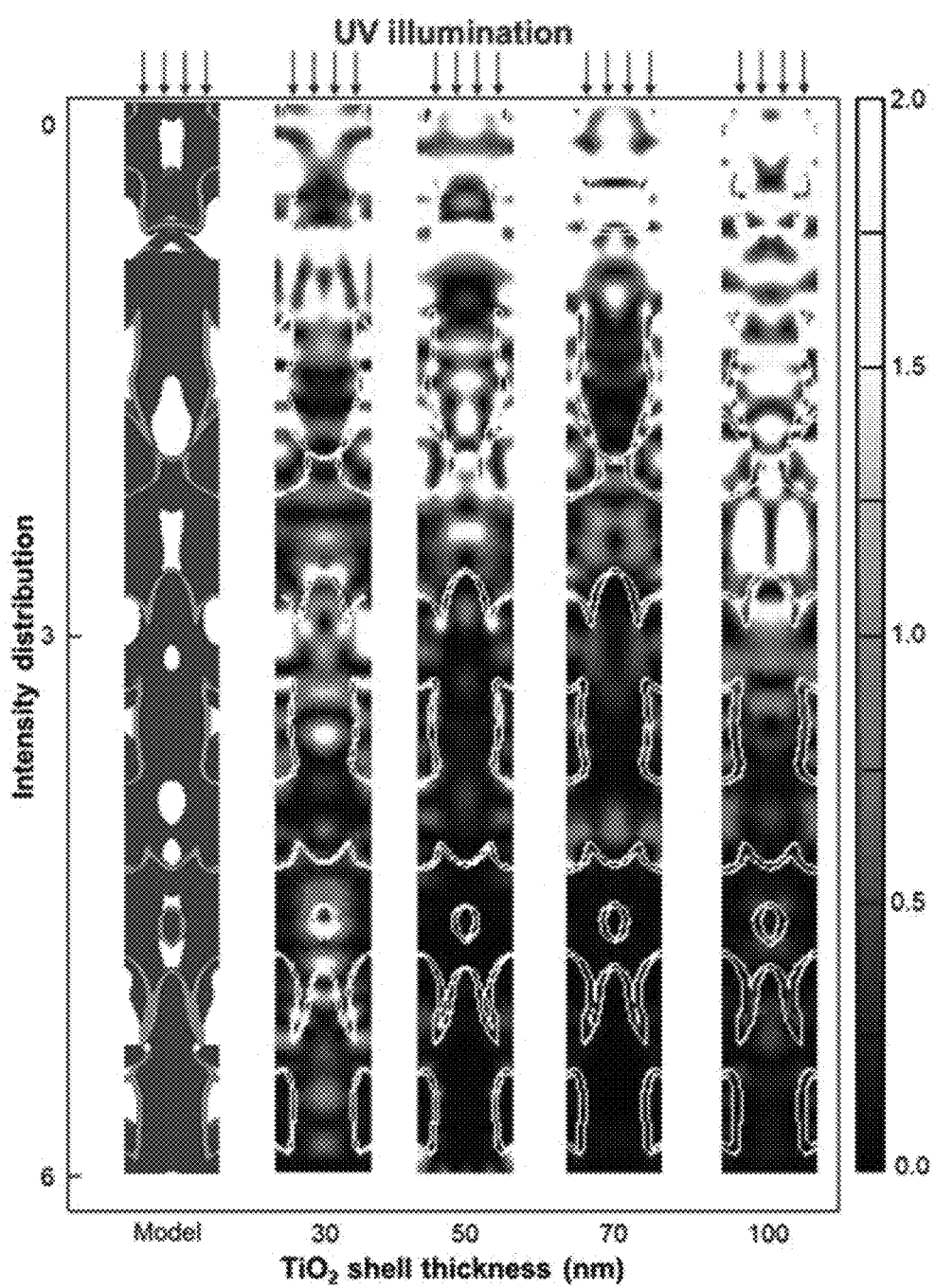
FIG. 12 is an optical simulation showing electromagnetic wave distribution of UV ray in the 3D porous sensitive members of Examples depending on shell thicknesses thereof.

FIG. 12 is an optical simulation showing electromagnetic wave distribution of UV ray in the 3D porous sensitive members of Examples depending on shell thicknesses thereof.

Referring to FIG. 12, it can be noted that light amplification and light-transferring effect may be changed depending on shell thicknesses of 3D porous sensitive members.

Figure 13:
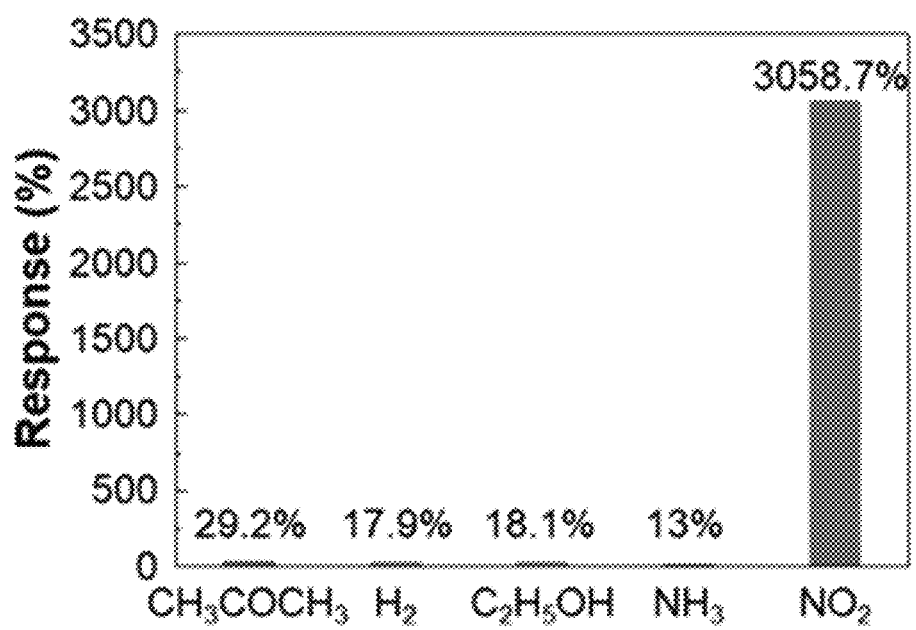
FIG. 13 is a graph showing sensitivities of the gas sensor according to Example (shell thickness of $TiO_2$: 30 nm, film thickness: 6 μm) to $CH_3COCH_3$, $H_2$, $C_2H_5OH$, $NH_3$ and $NO_2$.

FIG. 13 is a graph showing sensitivities of the gas sensor according to Example (shell thickness of $TiO_2$: 30 nm, film thickness: 6 μm) to $CH_3COCH_3$, $H_2$, $C_2H_5OH$, $NH_3$ and $NO_2$.

Referring to FIG. 13, it can be noted that the gas sensor according to Example may have selectivity for $NO_2$.

Figure 14:
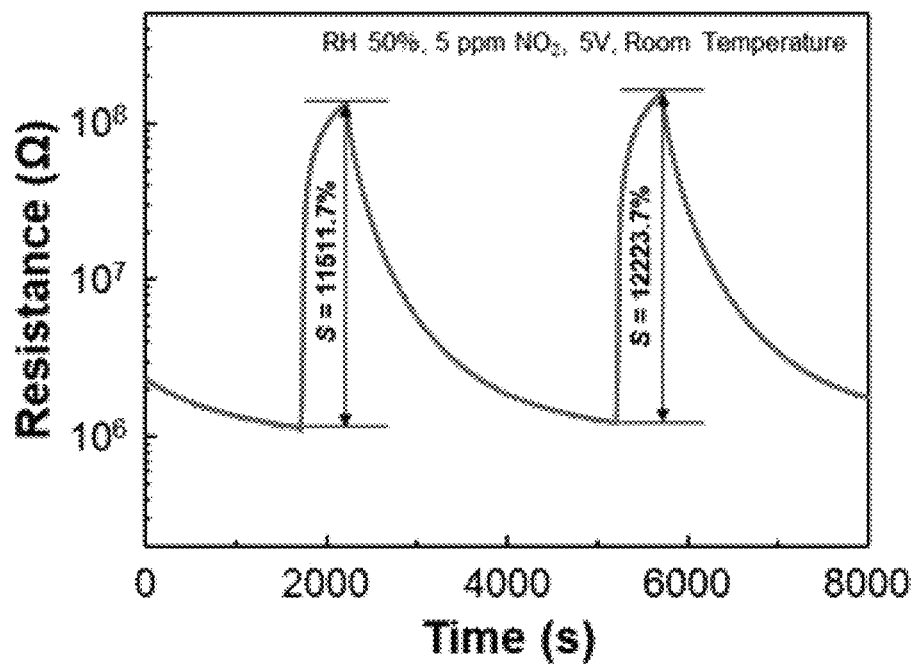
FIG. 14 a graph showing a response characteristic of the gas sensor according to Example (shell thickness of $TiO_2$: 30 nm, film thickness: 6 μm) in a humidity environment of RH 50% and at a room temperature.

FIG. 14 a graph showing a response characteristic of the gas sensor according to Example (shell thickness of $TiO_2$: 30 nm, film thickness: 6 μm) in a humidity environment of RH 50% and at a room temperature.

Referring to FIG. 14, it can be noted that the gas sensor according to Example may operate well at a low temperature and in a high-humidity environment.

Figure 15:
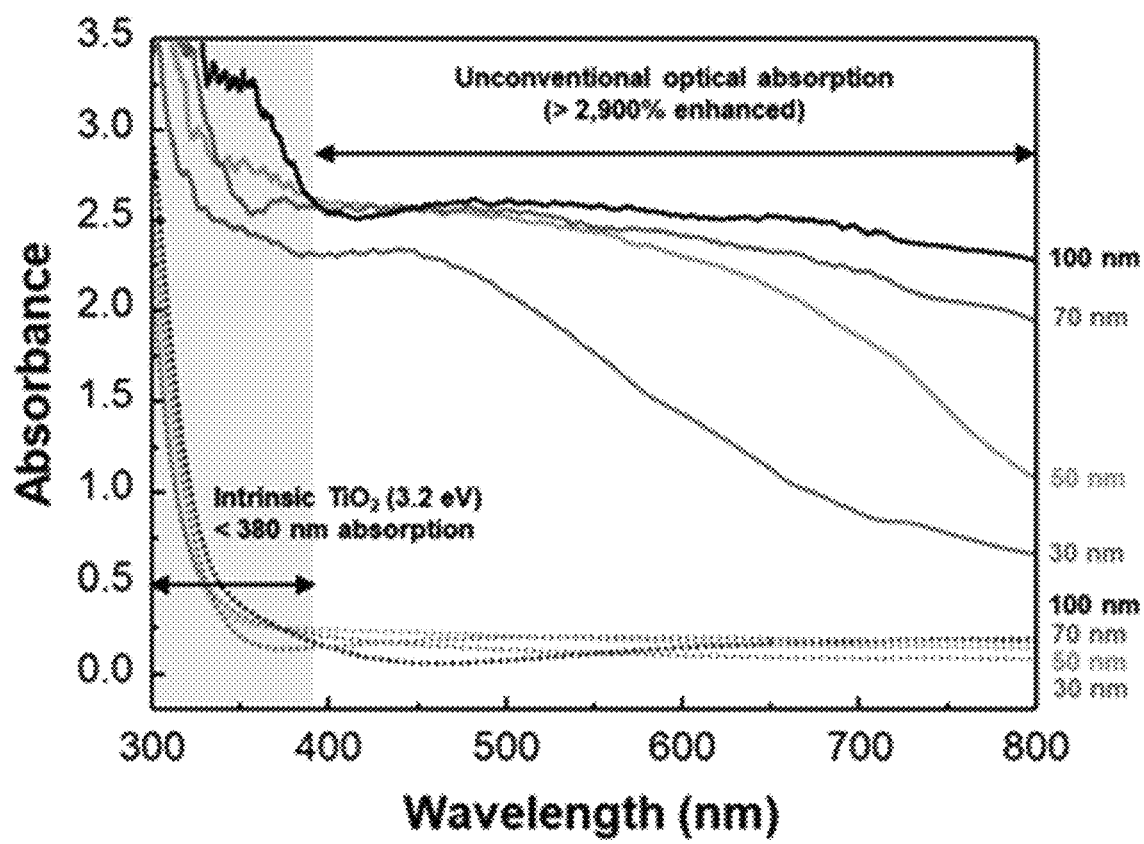
FIG. 15 is a graph showing optical absorption of the gas sensors according to Examples depending on shell thicknesses thereof.

FIG. 15 is a graph showing optical absorption of the gas sensors according to Examples depending on shell thicknesses thereof.

Referring to FIG. 15, it can be noted that nano-structured $TiO_2$ may have increased optical absorption with compared to bulky $TiO_2$ (intrinsic).

Figure 16:
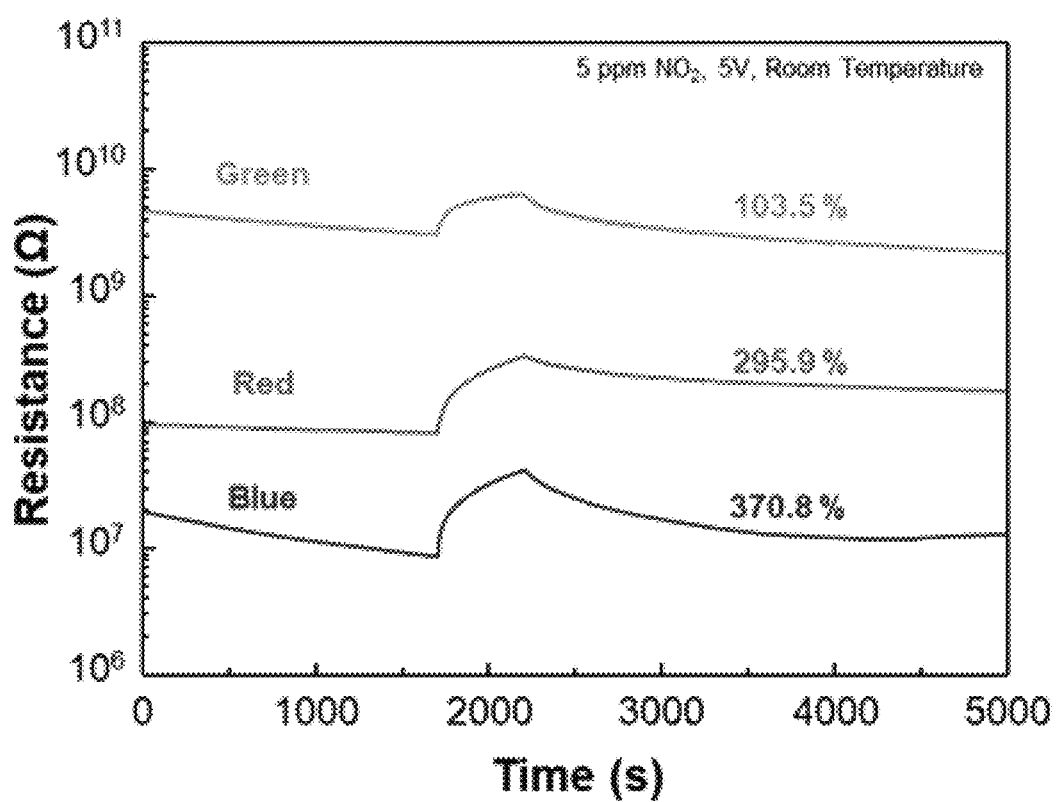
FIG. 16 is a graph showing electrical resistance of the gas sensors according to Examples to a red light (wavelength: 680 nm), a green light (wavelength: 532 nm) and a blue light (wavelength: 470 nm).

FIG. 16 is a graph showing electrical resistance of the gas sensors according to Examples to a red light (wavelength: 680 nm), a green light (wavelength: 532 nm) and a blue light (wavelength: 470 nm).

Referring to FIG. 16, it can be noted that the gas sensor according to Example may operate in response to a visible ray.

Gas sensors according to embodiments may be applied to hazards-detecting sensors for explosives, drugs, air-pollutants, organic volatile gases and the like.

The foregoing is illustrative of embodiments and is not to be construed as limiting thereof. Although a few embodiments have been described, those skilled in the art will readily appreciate that many modifications are possible in the embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various embodiments and is not to be construed as limited to the specific embodiments disclosed, and that modifications to the disclosed embodiments, as well as other embodiments, are intended to be included within the scope of the appended claims.

What is claimed is:

1. A light-activated gas sensor comprising:
   a first electrode disposed on a substrate;
   a second electrode disposed on the substrate and spaced apart from the first electrode; and
   a sensitive member disposed on the substrate and contacting the first and second electrodes and having a nano-shell structure with three-dimensional (3D) network shape, the nano-shell structure including a plurality of nano-shells respectively having a 3D layer shape to define and surround pores that are ordered with periodicity and connected to each other, the sensitive member including a metal oxide semiconductor as a gas-sensitive material,
   wherein a thickness of the sensitive member is 5 μm to 10 μm, and a thickness of the shells is 10 nm to 40 nm.

2. The light-activated gas sensor of claim 1, wherein the metal oxide semiconductor includes at least one of $SnO_2$, $ZnO$, $WO_3$, $Fe_2O_3$, $Fe_3O_4$, $NiO$, $TiO_2$, $CuO$, $In_2O_3$, $Zn_2SnO_4$, $Co_3O_4$, $PdO$, $LaCoO_3$, $NiCo_2O_4$, $Ca_2Mn_3O_8$, $V_2O_5$, $Ag_2V_4O_{11}$, $Ag_2O$, $MnO_2$, $InTaO_4$, $InTaO_4$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$ and $Ba_{0.5}Sr_{0.5}Co_{0.8}Fe_{0.2}O_3\text{-}\delta$.

3. The light-activated gas sensor of claim 1, wherein a porosity of the sensitive member is 90% or more.

4. A detection system comprising:
   a light-activated gas sensor of claim 1; and
   a light source irradiating a light to the light-activated gas sensor to activate the sensitive member.

* * * * *